United States Patent [19]

Hess et al.

[11] 4,010,270
[45] Mar. 1, 1977

[54] 4-OXO-4H-PYRANO[3,2-c]QUINOLINE-2-CARBOXYLIC ACIDS AND SALTS THEREOF

[75] Inventors: Friedrich Karl Hess, Pointe Fortune; Patrick Brian Stewart, St. Andrews East, both of Canada

[73] Assignee: Boehringer Ingelheim GmbH, Ingelheim am Rhein, Germany

[22] Filed: Sept. 23, 1975

[21] Appl. No.: 615,912

[30] Foreign Application Priority Data

Sept. 28, 1974 Germany .......................... 2446497

[52] U.S. Cl. .................. 424/258; 260/247.2 R; 260/287 R; 260/287 CE; 260/287 CF; 260/287 C; 260/287 AN; 260/289 K; 260/471 A; 260/578
[51] Int. Cl.² ........................................ C07D 491/04
[58] Field of Search ... 260/287 CF, 287 C, 247.2 R; 424/258

[56] References Cited

UNITED STATES PATENTS 3,629,290   12/1971   Cairns et al. ................ 260/287 CF

OTHER PUBLICATIONS

Elliott et al., "J. Chem. Soc," 1961 pp. 2796-2800; Chem. Abst. 56:1437i.

*Primary Examiner*—Donald G. Daus
*Assistant Examiner*—David E. Wheeler
*Attorney, Agent, or Firm*—Hammond & Littell

[57] ABSTRACT

Compounds of the formula

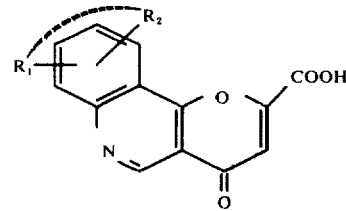

wherein $R_1$ and $R_2$, which may be identical to or different from each other, are each hydrogen, fluorine, chlorine, alkyl of 1 to 4 carbon atoms, phenyl, hydroxyl, alkoxy of 1 to 3 carbon atoms, alkylmercapto of 1 to 3 carbon atoms, hydroxycarbonyl or

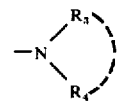

where $R_3$ and $R_4$ are each alkyl of 1 to 4 carbon atoms or, together with each other and the nitrogen atom to which they are attached, morpholino, piperidino, methylpiperidino or phenyl-piperidino; or $R_1$ and $R_2$, together with each other and adjacent carbon atoms of the benzene ring to which they are attached, —CH=CH—CH=CH—, —CH$_2$—CH$_2$—CH$_2$—CH$_2$— or —O—CH$_2$—O—;

and salts thereof. The compounds are useful as antiallergics.

7 Claims, No Drawings

4-OXO-4H-PYRANO[3,2-C]QUINOLINE-2-CAR-BOXYLIC ACIDS AND SALTS THEREOF

This invention relates to novel 4-oxo-4H-pyrano[3,2-c]quinoline-2-carboxylic acids and salts thereof, as well as to a method of preparing these compounds.

More particularly, the present invention relates to a novel class of 4-oxo-4H-pyrano[3,2-c]quinoline-2-carboxylic acids represented by the formula

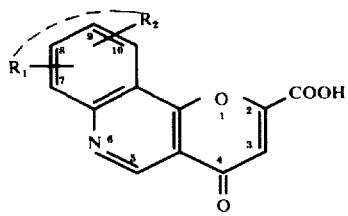

wherein $R_1$ and $R_2$, which may be identical to or different from each other, are each hydrogen, fluorine, chlorine, alkyl of 1 to 4 carbon atoms, phenyl, hydroxyl, alkoxy of 1 to 3 carbon atoms, alkylmercapto of 1 to 3 carbon atoms, hydroxycarbonyl or

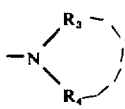

where $R_3$ and $R_4$ are each alkyl of 1 to 4 carbon atoms or, together with each other and the nitrogen atom to which they are attached, morpholino, piperidino, methylpiperidino or phenyl-piperidino; or $R_1$ and $R_2$, together with each other and adjacent carbon atoms of the benzene ring to which they are attached, —CH=CH—CH=CH—, —CH$_2$—CH$_2$—CH$_2$—CH$_2$— or —O—CH$_2$—O—;

and salts thereof.

The compounds embraced by formula I may be prepared by subjecting a 3-alkanoyl-4-hydroxy-quinoline of the formula

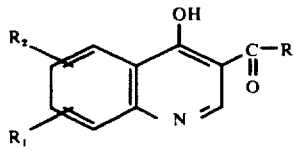

wherein $R_1$ and $R_2$ have the same meanings as in formula I, and

R is lower alkyl, to a condensation reaction with a lower alkyl oxalate to form an intermediate of the formula

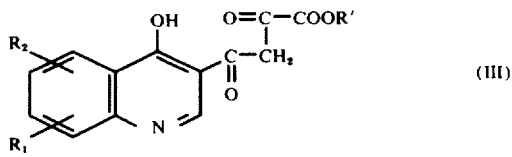

wherein $R_1$ and $R_2$ have the same meanings as in formula I, and

R' is lower alkyl, and subsequently subjecting the said intermediate to a ring closure reaction, optionally accompanied by simultaneous hydrolysis.

The condensation reaction is carried out in the presence of metallic sodium or potassium, or also in the presence of sodium amide, sodium hydride or potassium tert. butylate, and in an inert organic solvent medium, such as a lower alkanol, toluene, tetahydrofuran or dioxane, whereby the sodium or potassium salt of the quinoline starting compound of the formula II is initially formed; the said sodium or potassium salt then reacts in situ, accompanied by heating, with the oxalic acid ester to form the intermediate of the formula III.

The subsequent ring closure of the intermediate is effected by means of heating the same with a mineral acid, preferably with a mixture of glacial acetic acid and concentrated hydrochloric acid. It is not absolutely essential that the intermediate of the formula III be isolated prior to subjecting it to ring closure; in other words, the ring closure may be effected in situ in the reaction solution resulting from the condensation reaction.

An end product of the formula I may, if desired, be converted into a salt thereof, especially into an addition salt thereof, such as the ethanolamine salt. For this purpose the carboxylic acid is dissolved or suspended in water, and the desired base is added to the aqueous solution or suspension until it has a pH of 7. For isolation of the salt, the resulting solution is preferably freeze-dried, because evaporation of the solution may in some instances cause decomposition of the desired end product.

The starting compounds of the formula II may, for example, be prepared by reacting an aniline of the formula

wherein $R_1$ and $R_2$ have the meanings previously defined, with a 2-ethoxymethylene lower alkyl acetoacetate while heating, optionally under reduced pressure, to form an intermediate of the formula

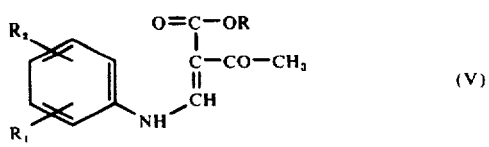

wherein $R_1$, $R_2$ and R have the meanings previously defined, and subsequently subjecting the intermediate to ring closure in a high-boiling-point solvent, such as diphenyl ether, tetrahydronaphthalene, diphenyl or a chlorinated aromatic hydrocarbon.

Examples of end products of the formula I, optionally in the form of a salt thereof, which may be prepared in the manner described above are the following:

4-Oxo-7-methoxy-4H-pyrano[3,2-c]quinoline-2-carboxylic acid,
4-Oxo-7-methyl-4H-pyrano[3,2-c]quinoline-2-carboxylic acid,
4-Oxo-7-methylmercapto-4H-pyrano[3,2-c]quinoline-2-carboxylic acid,
4-Oxo-7-phenyl-4H-pyrano[3,2-c]quinoline-2-carboxylic acid,
4-Oxo-7-piperidino-4H-pyrano[3,2-c]quinoline-2-carboxylic acid,
4-Oxo-7-morpholino-4H-pyrano[3,2-c]quinoline-2-carboxylic acid,
4-Oxo-8-hydroxy-4H-pyrano[3,2-c]quinoline-2-carboxylic acid,
4-Oxo-8-methoxy-4H-pyrano[3,2-c]quinoline-2-carboxylic acid,
4-Oxo-8-methylmercapto-4H-pyrano[3,2-c]quinoline-2-carboxylic acid,
4-Oxo-8chloro-4H-pyrano[3,2-c]quinoline-2-carboxylic acid,
4-Oxo-8-methyl-4H-pyrano[3,2-c]quinoline-2-carboxylic acid,
4-Oxo-8-ethyl-4H-pyrano[3,2-c]quinoline-2-carboxylic acid,
4-Oxo-8-phenyl-4H-pyrano[3,2-c]quinoline-2-carboxylic acid,
4-Oxo-8-dimethylamino-4H-pyrano[3,2-c]quinoline-2-carboxylic acid,
4-Oxo-9-methoxy-4H-pyrano[3,2-c]quinoline-2-carboxylic acid,
4-Oxo-9-methyl-4H-pyrano[3,2-c]quinoline-2-carboxylic acid,
4-Oxo-8,9-dimethyl-4H-pyrano[3,2-c]quinoline-2-carboxylic acid,
4-Oxo-8-chloro-9-methyl-4H-pyrano[3,2-c]quinoline-2-carboxylic acid,
4-Oxo-9-ethyl-4H-pyrano[3,2-c]quinoline-2-carboxylic acid,
4-Oxo-9-isopropyl-4H-pyrano[3,2-c]quinoline-2-carboxylic acid,
4-Oxo-9-n-butyl-4H-pyrano[3,2-c[quinoline-2-carboxylic acid,
4-Oxo-9-methylmercapto-4H-pyrano[3,2-quinoline-2-carboxylic acid,
4-Oxo-9-fluoro-4H-pyrano[3,2-c]quinoline-2-carboxylic acid,
4-Oxo-9-chloro-4H-pyrano[3,2-c]quinoline-2-carboxylic acid,
4-Oxo-9-phenyl-4H-pyrano[3,2-c]quinoline-2-carboxylic acid,
4-Oxo-9-hydroxycarbonyl-4H-pyrano[3,2-c]quinoline-2-carboxylic acid,
4-Oxo-9-di-(n-butyl)-amino-4H-pyrano[3,2-c]quinoline-2-carboxylic acid,
4-Oxo-9-(4-methylpiperidino)-4H-pyrano[3,2-c]quinoline-2-carboxylic acid,
4-Oxo-9-morpholino-4H-pyrano[3,2-c]quinoline-2-carboxylic acid,
4-Oxo-9-(4-phenylpiperidino)-4H-pyrano[3,2-c]quinoline-2-carboxylic acid,
4-Oxo-8,10-dimethoxy-4H-pyrano[3,2-c]quinoline-2-carboxylic acid,
4-Oxo-8,10-dimethyl-4H-pyrano[3,2-c]quinoline-2-carboxylic acid,
4-Oxo-4H-pyrano[3,2-c]quinoline-2-carboxylic acid,
4-Oxo-4H-benzo-[f]-pyrano[3,2-c]quinoline-2-carboxylic acid,
7,8,9,10-tetrahydro-1-oxo-1H-benzo-[h]-pyrano[3,2-c]quinoline-3-carboxylic acid,
1-Oxo-1H-benzo-[h]-pyrano[3,2-c]quinoline-3-carboxylic acid, and
4-Oxo-8,9-dioxymethylene-4H-pyrano[3,2-c]quinoline-2-carboxylic acid.

The following examples illustrate the present invention and will enable others skilled in the art to understand it more completely. It should be understood, however, that the invention is not limited solely to the particular examples given below.

EXAMPLE 1

4-Oxo-7-methoxy-4H-pyrano[3,2-c]quinoline-2-carboxylic acid and its ethanolamine salt A mixture of 18 gm of metallic sodium and 330 ml of ethanol was refluxed for a short period of time, while stirring, and the resulting sodium ethylate solution was allowed to cool. Thereafter, a mixture consisting of 15 gm of 3-acetyl-4-hydroxy-8-methoxy-quinoline, 27 gm of diethyl oxalate and 430 ml of ethanol was added to the sodium ethylate solution, and the resulting mixture was refluxed for 30 minutes. Subsequently, the reaction mixture was allowed to cool and was then filtered, and the filter cake was dried in vacuo at 70° C overnight. It was identified to be the intermediate condensation product of the formula III ($R_1 = 8—OCH_3$, $R_2 = H$, $R' = —C_2H_5$).

The intermediate was added to a mixture consisting of 190 ml of glacial acetic acid and 85 ml of aqueous 37% hydrochloric acid, and the resulting mixture was refluxed for three hours. Thereafter, the reaction mixture was allowed to cool, the precipitated inorganic salts were removed by filtration, and the filtrate was poured into ice water. The precipitate formed thereby was collected, washed with water, dried over phosphorus pentoxide, recrystallized from hot dimethylformamide, and washed with acetone, yielding 6.2 gm (33% of theory) of 4-oxo-7-methoxy-4H-pyrano[3,2-c]quinoline-2-carboxylic acid of the formula

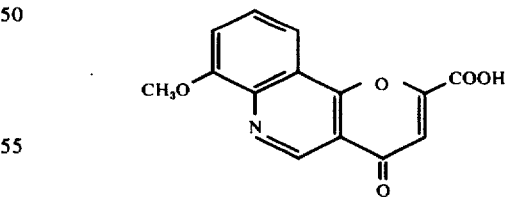

Its ethanolamine salt, obtained by dissolving the free acid in water and adding ethanolamine to the solution until it had a pH of 7, had a melting point of 257° C.

The starting compound, 3-acetyl-4-hydroxy-8-methoxy-quinoline, was obtained as follows:

a. 93 gm of 2-ethoxymethylene ethyl acetoacetate were added slowly to 61.5 gm of o-methoxy-aniline at a temperature between 40° and 50° C, and the resulting mixture was heated for 45 minutes at 130° C under reduced pressure. Thereafter, the reaction mixture was allowed to cool, and the precipitate formed thereby was collected, yielding 121 gm (91% of theory) of the compound of the formula V ($R_1 = H$, $R_2 = o-OCH_3$) which had a melting point of 107°–108° C (from hexane/chloroform).

b. 300 ml of diphenyl ether were heated to about 230° C, and 40 gm of the end product obtained in (a) were added at that temperature, while stirring. The temperature of the mixture was then increased to 260° C and maintained until the reaction had gone to completion. Thereafter, the reaction solution was allowed to cool, and the precipitate formed thereby was filtered off, washed with diethyl ether, crystallized from hot dimethylformamide, again filtered off and washed with diethyl ether, yielding 20.4 gm (60.6% of theory) of the desired compound which had a melting point of 293°–294° C.

EXAMPLE 2

Using a procedure analogous to that described in Example 1, 4-oxo-4H-pyrano[3,2-c]quinoline-2-carboxylic acid, m.p. 304°–305° C, was prepared from 3-acetyl-4-hydroxy-quinoline and diethyl oxalate.

EXAMPLE 3

Using a prodcedure analogous to that described in Example 1, 4-oxo-7-methyl-4H-pyrano[3,2-c]quinoline-2-carboxylic acid, m.p. 295°–296° C, was prepared from 3-acetyl-4-hydroxy-8-methyl-quinoline and diethyl oxalate.

EXAMPLE 4

Using a procedure analogous to that described in Example 1, 4-oxo-8-methyl-4H-pyrano[3,2-c]quinoline-2-carboxylic acid, m.p. 280°–281° C, was prepared from 3-acetyl-4-hydroxy-7-methyl-quinoline and diethyl oxalate.

EXAMPLE 5

Using a procedure analogous to that described in Example 1, 4-oxo-9-methyl-4H-pyrano[3,2-c]quinoline-2-carboxylic acid, m.p. 284° C, was prepared from 3-acetyl-4-hydroxy-6-methyl-quinoline and diethyl oxalate.

EXAMPLE 6

Using a procedure analogous to that described in Example 1, 4-oxo-8,9-dimethyl-4H-pyrano[3,2-c]quinoline-2carboxylic acid, m.p. 279° C, was prepared from 3-acetyl-4-hydroxy-6,7-dimethyl-quinoline and diethyl oxalate.

EXAMPLE 7

Using a procedure analogous to that described in Example 1, 4-oxo-8,10-dimethyl-4H-pyrano[3,2-c]quinoline-2-carboxylic acid, m.p. 299.5°–300.5° C, was prepared from 3-acetyl-4-hydroxy-5,7-dimethyl-quinoline and diethyl oxalate.

EXAMPLE 8

Using a procedure analogous to that described in Example 1, 4-oxo-8-ethyl-4H-pyrano[3,2-c]quinoline-2-carboxylic acid, m.p. 288° C, was prepared from 3-acetyl-4-hydroxy-7-ethyl-quinoline and diethyl oxalate.

EXAMPLE 9

Using a procedure analogous to that described in Example 1, 4-oxo-9-ethyl-4H-pyrano[3,2-c]quinoline-2-carboxylic acid, m.p. 273°–274° C, was prepared from 3-acetyl-4-hydroxy-6-ethyl-quinoline and diethyl oxalate.

EXAMPLE 10

Using a procedure analogous to that described in Example 1, 4-oxo-9-isopropyl-4H-pyrano[3,2-c]quinoline-2-carboxylic acid, m.p. 279° C, was prepared from 3-acetyl-4-hydroxy-6-isopropyl-quinoline and diethyl oxalate.

EXAMPLE 11

Using a procedure analogous to that described in Example 1, 4-oxo-9-(n-butyl)-4H-pyrano[3,2-c]quinoline-2-carboxylic acid, m.p. 268° C, was prepared from 3-acetyl-4hydroxy-6-(n-butyl)-quinoline and diethyl oxalate.

EXAMPLE 12

Using a procedure analogous to that described in Example 1, 4-oxo-8-methoxy-4H-pyrano[3,2-c]quinoline-2-carboxylic acid, m.p. 283° C, was prepared from 3-acetyl-4-hydroxy-7-methoxy-quinoline and diethyl oxalate.

EXAMPLE 13

Using a procedure analogous to that described in Example 1, 4-oxo-9-methoxy-4H-pyrano[3,2-c]quinoline-2-carboxylic acid, m.p. 200°–202° C, was prepared from 3-acetyl-4-hydroxy-6-methoxy-quinoline and diethyl oxalate.

EXAMPLE 14

Using a procedure analogous to that described in Example 1, 4-oxo-8,10-dimethoxy-4H-pyrano[3,2-c]quinoline-2-carboxylic acid, m.p. 308°–309° C, was prepared from 3-acetyl-4-hydroxy-5,7-dimethoxy-quinoline and diethyl oxalate.

EXAMPLE 15

Using a procedure analogous to that described in Example, 1, 4-oxo-7-methylmercapto-4H-pyrano[3,2-c]quinoline-2-carboxylic acid, m.p. 292° C, was prepared from 3-acetyl-4-hydroxy-8-methylmercapto-quinoline and diethyl oxalate.

EXAMPLE 16

Using a procedure analogous to that described in Example 1, 4-oxo-8-methylmercapto-4H-pyrano[3,2-c]quinoline-2-carboxylic acid, m.p. 281° C, was prepared from 3-acetyl-4-hydroxy-7-methylmercapto-quinoline and diethyl oxalate.

EXAMPLE 17

Using a procedure analogous to that described in Example 1, 4-oxo-9-methylmercapto-4H-pyrano[3,2-c]quinoline-2-carboxylic acid, m.p. 277°–278° C, was prepared from 3-acetyl-4-hydroxy-6-methylmercapto-quinoline and diethyl oxalate.

EXAMPLE 18

Using a procedure analogous to that described in Example 1, 4-oxo-8-hydroxy-4H-pyrano[3,2-c]quinoline-2-carboxylic acid, m.p.~310° C, was prepared from 3-acetyl-4,7-di-hydroxy-quinoline and diethyl oxalate.

EXAMPLE 19

Using a procedure analogous to that described in Example 1, 4-oxo-9-fluoro-4H-pyrano[3,2-c]quinoline-2-carboxylic acid, m.p. 284°–285° C, was prepared from 3-acetyl-4-hydroxy-6-fluoro-quinoline and diethyl oxalate.

EXAMPLE 20

Using a procedure analogous to that described in Example 1, 4-oxo-8-chloro-4H-pyrano[3,2-c]quinoline-2-carboxylic acid, m.p. 289°–290° C, was prepared from 3-acetyl-4-hydroxy-7-chloro-quinoline and diethyl oxalate.

EXAMPLE 21

Using a procedure analogous to that described in Example 1, 4-oxo-9-chloro-4H-pyrano[3,2-c]quinoline-2-carboxylic acid, m.p. 286°–287° C, was prepared from 3-acetyl-4-hydroxy-6-chloro-quinoline and diethyl oxalate.

EXAMPLE 22

Using a procedure analogous to that described in Example 1, 4-oxo-8-chloro-9-methyl-4H-pyrano[3,2-c]quinoline-2-carboxylic acid, m.p. 274° C, was prepared from 3-acetyl-4-hydroxy-6-methyl-7-chloroquinoline and diethyl oxalate.

EXAMPLE 23

Using a procedure analogous to that described in Example 1, 4-oxo-9-hydroxycarbonyl-4H-pyrano[3,2-c]quinoline-2-carboxylic acid, m.p. 297°–300° C, was prepared from 3-acetyl-4-hydroxy-6-hydroxycarbonyl-quinoline and diethyl oxalate.

EXAMPLE 24

Using a procedure analogous to that described in Example 1, 4-oxo-8-dimethylamino-4H-pyrano[3,2-c]quinoline-2-carboxylic acid, m.p. 288° C, was prepared from 3-acetyl-4-hydroxy-7-dimethylaminoquinoline and diethyl oxalate.

EXAMPLE 25

Using a procedure analogous to that described in Example 1, 4-oxo-9-dibutylamino-4H-pyrano[3,2-c]quinoline-2-carboxylic acid, m.p. 276°–277° C, was prepared from 3-acetyl-4-hydroxy-6-dibutylaminoquinoline and diethyl oxalate.

EXAMPLE 26

Using a procedure analogous to that described in Example 1, 4-oxo-7-piperidino-4H-pyrano[3,2-c]quinoline-2-carboxylic acid · ¼ $H_2O$, m.p. ~190° C, was prepared from 3-acetyl-4-hydroxy-8-piperidinoquinoline and diethyl oxalate.

EXAMPLE 27

Using a procedure analogous to that described in Example 1, 4-oxo-9-(4'-methyl-piperidino)-4H-pyrano[3,2-c]quinoline-2-carboxylic acid, m.p. 282°–284° C of the formula

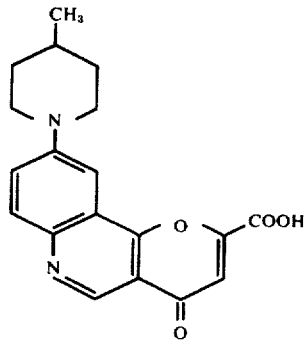

was prepared from 3-acetyl-4-hydroxy-6-(4'-methyl-piperidino)-quinoline and diethyl oxalate.

EXAMPLE 28

Using a procedure analogous to that described in Example 1, 4-oxo-7-morpholino-4H-pyrano[3,2-c]quinoline-2-carboxylic acid, m.p. 256°–257° C, was prepared from 3-acetyl-4-hydroxy-8-morpholinoquinoline and diethyl oxalate.

EXAMPLE 29

Using a procedure analogous to that described in Example 1, 4-oxo-9-morpholino-4H-pyrano[3,2-c]quinoline-2-carboxylic acid, m.p. 289° C, was prepared from 3-acetyl-4-hydroxy-6-morpholino-quinoline and diethyl oxalate.

EXAMPLE 30

Using a procedure analogous to that described in Example 1, 4-oxo-7-phenyl-4H-pyrano[3,2-c]quinoline-2-carboxylic acid, m.p. 274°–276° C, was prepared from 3-acetyl-4-hydroxy-8-phenyl-quinoline and diethyl oxalate.

EXAMPLE 31

Using a procedure analogous to that described in Example 1, 4-oxo-8-phenyl-4H-pyrano[3,2-c]quinoline-2-carboxylic acid, m.p. 285° C, was prepared from 3-acetyl-4-hydroxy-7-phenyl-quinoline and diethyl oxalate.

EXAMPLE 32

Using a procedure analogous to that described in Example 1, 4-oxo-9-phenyl-4H-pyrano[3,2-c]quinoline-2-carboxylic acid, m.p. 283° C, was prepared from 3-acetyl-4-hydroxy-6-phenyl-quinoline and diethyl oxalate.

EXAMPLE 33

Using a procedure analogous to that described in Example 1, 4-oxo-8,9-methylenedioxy-4H-pyrano[3,2-c]quinoline-2-carboxylic acid, m.p. 293°–295° C, of the formula

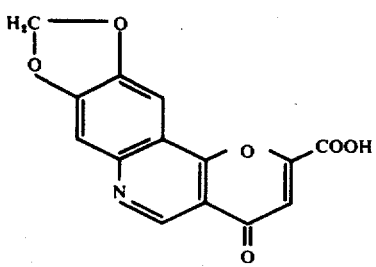

was prepared from 3-acetyl-4-hydroxy-6,7-methylene-dioxy-quinoline and diethyl oxalate.

EXAMPLE 34

Using a procedure analogous to that described in Example 1, 7,8,9,10-tetrahydro-1-oxo-1H-benzo[h]pyrano[3,2-c]-quinoline-3-carboxylic acid, m.p. 279°–280° C, of the formula

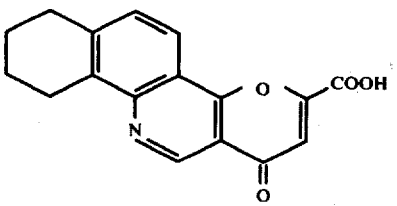

was prepared from 3-acetyl-4-hydroxy-7,8-tetramethylene-quinoline and diethyl oxalate.

EXAMPLE 35

Using a procedure analogous to that described in Example 1, 1-oxo-1H-benzo[h]pyrano[3,2-c]quinoline-3-carboxylic acid, m.p. 298° C, of the formula

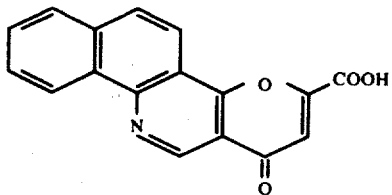

was prepared from 3-acetyl-4-hydroxy-benzo[h]quinoline and diethyl oxalate.

EXAMPLE 36

Using a procedure analogous to that described in Example 1, 4-oxo-4H-benzo[f]pyrano 3,2-c]quinoline-2-carboxylic acid, m.p.~203° C, of the formula

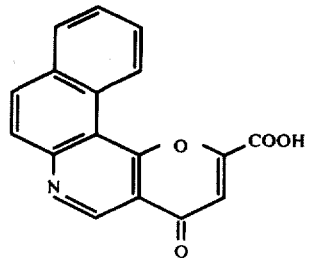

was prepared from 3-acetyl-4-hydroxy-benzo[f]quinoline and diethyl oxalate.

The compounds of the present invention, that is, those embraced by formula I above and their non-toxic, pharmacologically acceptable salts, especially their ethanolamine salts, have useful pharmacodynamic properties. More particularly, they exhibit antiallergic activity in warm-blooded animals, such as monkeys, and are therefore useful for the treatment of allergic asthma, hay fever, hives, eczema, atopical dermatitides and other allergic conditions.

Particularly effective are 4-oxo-7-methoxy-4H-pyrano [3,2-c]quinoline-2-carboxylic acid and 4-oxo-8-methylmercapto-4H-pyrano[3,2-c]quinoline-2-carboxylic acid and their non-toxic salts. For example, in the monkey-asthma-model, 4-oxo-7-methoxy-4H-pyrano[3,2-c]quinoline-2-carboxylic acid reduces the increase in airway resistance from 50 to 6%, following bronchial challenge with the appropriate allergen.

In addition, the compounds of the present invention exhibit extremely low toxicities. For instance, the $LD_{50}$ (p.o. as well as i.v.) of 4-oxo-7-methoxy-4H-pyrano[3,2-c]quinoline-2-carboxylic acid exceeds 2000 mgm/kg (mouse).

For pharmaceutical purposes the compounds according to the present invention are administered to warm-blooded animals topically, perorally, parenterally or by the respiratory route as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, inhalation aerosols, ointments, emulsions, syrups, suppositories and the like. One effective parenteral or inhalation dosage unit of the compounds according to the present invention is from 0.083 to 0.84 mgm/kg body weight, and the peroral dosage range is from 0.83 to 8.4 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 37

Tablets

The tablet composition is compounded from the following ingredients:

| | |
|---|---|
| Ethanolamine salt of 4-oxo-7-methoxy-4H-pyrano[3,2-c]quinoline-2-carboxylic acid | 0.100 parts |
| Stearic acid | 0.010 parts |

-continued

| | |
|---|---|
| Dextrose | 1.890 parts |
| Total | 2.000 parts |

Preparation

The ingredients are admixed in conventional manner, and the mixture is compressed into 2.0 gm-tablets, each of which contains 100 mgm of the pyranoquinoline-carboxylic acid salt and is an oral dosage unit composition with effective antiallergic action.

EXAMPLE 38

Ointment

The ointment composition is compounded from the following ingredients:

| | |
|---|---|
| Ethanolamine salt of 4-oxo-7-methoxy-4H-pyrano[3,2-c]quinoline-2-carboxylic acid | 2.000 parts |
| Fuming hydrochloric acid | 0.011 parts |
| Sodium pyrosulfite | 0.050 parts |
| Mixture (1:1) of cetyl alcohol and stearyl alcohol | 20.000 parts |
| White vaseline | 5.000 parts |
| Synthetic bergamot oil | 0.075 parts |
| Distilled water q.s.ad | 100.000 parts |

Preparation

The ingredients are uniformly blended in conventional manner into an ointment, 100 gm of which contain 2.0 gm of the pyranoquinoline-carboxylic acid salt. The ointment is an effective antiallergic composition for topical application.

EXAMPLE 39

Inhalation aerosol

The aerosol composition is compounded from the following ingredients:

| | |
|---|---|
| 4-Oxo-7-methoxy-4H-pyrano[3,2-c]quinoline-2-carboxylic acid | 1.00 parts |
| Soybean lecithin | 0.20 parts |
| Propellent gas mixture (frigen 11, 12 and 14) q.s.ad | 100.00 parts |

Preparation

The ingredients are compounded in conventional manner, and the composition is filled into aerosol containers with a metering valve which releases 5 to 20 mgm of active ingredient per actuation of the valve. The aerosol spray a dosage unit composition with effective antiallergic action for administration by the respiratory route.

EXAMPLE 40

Hypodermic solution

The solution is compounded from the following ingredients:

| | |
|---|---|
| Ethanolamine salt of 4-oxo-8-methyl-mercapto-4H-pyrano[3,2-c]quinoline-2-carboxylic acid | 50.0 parts |
| Sodium pyrosulfite | 1.0 parts |
| Sodium salt of EDTA | 0.5 parts |
| Sodium chloride | 8.5 parts |
| Double-distilled water q.s.ad | 1000.0 parts |

Preparation

The individual ingredients are dissolved in a sufficient amount of double-distilled water, the solution is diluted to the indicated concentration with additional double-distilled water, the resulting solution is filtered until free from suspended particles, and the filtrate is filled under aseptic conditions into 1 ml-ampules which are subsequently sterilized and sealed. Each ampule contains 50 mgm of the pyranoquinoline-carboxylic acid salt, and the contents thereof are an injectable dosage unit composition with effective antiallergic action.

Analogous results are obtained when any one of the other pyranoquinoline-carboxylic acids embraced by formula 1 or a non-toxic salt thereof is substituted for the particular active ingredient in Examples 37 through 40. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

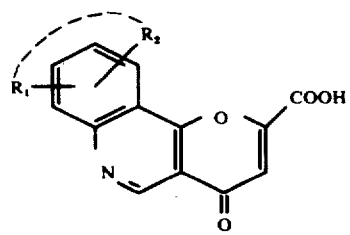

wherein
R₁ is alkyl of 1 to 4 carbon atoms, alkoxy of 1 to 3 carbon atoms, fluorine or chlorine,
R₂ is alkyl of 1 to 4 carbon atoms, alkoxy of 1 to 3 carbon atoms, fluorine, chlorine, phenyl, hydroxyl, alkyl of 1 to 3 carbon atoms-mercapto, carboxyl or

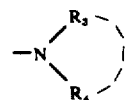

where
R₃ and R₄ are each alkyl of 1 to 4 carbon atoms or, together with each other and the nitrogen atom to which they are attached, morpholino, piperidino or methyl-piperidino; or $R_1$ and $R_2$, together with each other and when attached to adjacent carbon atoms of the benzene ring, are —CH=CH—CH=CH, —CH$_2$—CH$_2$—CH$_2$—CH$_2$— or —O—CH$_2$—O—;

or a non-toxic, pharmacologically acceptable salt thereof.

2. A compound of claim 1, which is 4-oxo-7-methoxy-4H-pyrano[3,2-c]quinoline-2-carboxylic acid or a non-toxic, pharmacologically acceptable salt thereof.

3. A compound of claim 1, which is 4-oxo-7-methylmercapto-4H-pyrano[3,2-c]quinoline-2-carboxylic acid or a non-toxic, pharmacologically acceptable salt thereof.

4. A compound of claim 1, which is 4-oxo-9-morpholino- 4H-pyrano[3,2-c]quinoline-2-carboxylic acid or a non-toxic, pharmacologically acceptable salt thereof.

5. A compound of claim 1, which is 4-oxo-8-isopropyl- 4H-pyrano[3,2-c]quinoline-2-carboxylic acid or a non-toxic, pharmacologically acceptable salt thereof.

6. An antiallergic pharmaceutical dosage unit composition consisting essentially of an inert pharmaceutical carrier and an effective antiallergic amount of a compound of claim 1.

7. The method of suppressing allergic reactions in a warm-blooded animal, which comprises administering topically, perorally, parenterally or by the respiratory route to said animal an effective antiallergic amount of claim 1.

* * * * *